(12) United States Patent
Alberico et al.

(10) Patent No.: US 9,388,135 B2
(45) Date of Patent: Jul. 12, 2016

(54) PROCESS FOR PREPARING N-BENZYL-3-HYDROXY-4-SUBSTITUTED-PYRIDIN-2-(1H)-ONES

(71) Applicant: Aerpio Therapeutics, Inc., Cincinnati, OH (US)

(72) Inventors: Dino Alberico, Mississauga (CA); Craig Dixon, Brooklin (CA); Boris Gorin, Oakville (CA); Jan Oudenes, Aurora (CA)

(73) Assignee: AERPIO THERAPEUTICS, INC., Cincinnati, OH (US)

( * ) Notice: Subject to any disclaimer, the term of this patent is extended or adjusted under 35 U.S.C. 154(b) by 0 days.

(21) Appl. No.: 14/624,625

(22) Filed: Feb. 18, 2015

(65) Prior Publication Data

US 2015/0232425 A1 Aug. 20, 2015

Related U.S. Application Data

(60) Provisional application No. 61/941,540, filed on Feb. 19, 2014.

(51) Int. Cl.
*C07D 213/69* (2006.01)

(52) U.S. Cl.
CPC ............. *C07D 213/69* (2013.01); *Y02P 20/55* (2015.11)

(58) Field of Classification Search
CPC .............................. Y02P 20/55; C07D 213/69
See application file for complete search history.

(56) References Cited

U.S. PATENT DOCUMENTS

| | | | |
|---|---|---|---|
| 4,508,898 A | 4/1985 | Ogilvie | |
| 6,930,117 B2 | 8/2005 | Warshakoon et al. | |
| 6,946,479 B2 | 9/2005 | Warshakoon et al. | |
| 7,226,755 B1 | 6/2007 | Peters et al. | |
| 7,247,632 B2 | 7/2007 | Warshakoon et al. | |
| 7,247,648 B2 | 7/2007 | Warshakoon et al. | |
| 7,507,568 B2 | 3/2009 | Evdokimov et al. | |
| 7,589,212 B2 | 9/2009 | Gray et al. | |
| 7,622,593 B2 | 11/2009 | Gray et al. | |
| 7,632,862 B2 | 12/2009 | Peters et al. | |
| 7,769,575 B2 | 8/2010 | Evdokimov et al. | |
| 7,790,748 B2 | 9/2010 | Warshakoon et al. | |
| 7,795,444 B2 | 9/2010 | Gray et al. | |
| 7,973,142 B2 | 7/2011 | Rotello et al. | |
| 8,106,078 B2 | 1/2012 | Gray et al. | |
| 8,133,894 B2 | 3/2012 | Warshakoon et al. | |
| 8,188,125 B2 | 5/2012 | Gray et al. | |
| 8,258,311 B2 | 9/2012 | Gray et al. | |
| 8,309,537 B2 | 11/2012 | Gardner et al. | |
| 8,323,671 B2 | 12/2012 | Wu et al. | |
| 8,329,916 B2 | 12/2012 | Gray et al. | |
| 8,338,615 B2 | 12/2012 | Gray et al. | |
| 8,524,235 B2 | 9/2013 | Rotello et al. | |
| 8,536,181 B2 | 9/2013 | Gardner et al. | |
| 8,569,348 B2 | 10/2013 | Shalwitz et al. | |
| 8,778,412 B2 | 7/2014 | Shalwitz et al. | |
| 8,846,685 B2 | 9/2014 | Gray et al. | |
| 8,883,774 B2 | 11/2014 | Shalwitz et al. | |
| 8,883,832 B2 | 11/2014 | Shalwitz et al. | |
| 8,895,563 B2 | 11/2014 | Gray et al. | |
| 8,946,232 B2 | 2/2015 | Gray et al. | |
| 8,999,325 B2 | 4/2015 | Peters et al. | |
| 8,999,971 B2 | 4/2015 | Shalwitz et al. | |
| 9,045,495 B2 | 6/2015 | Gardner et al. | |
| 2004/0077065 A1 | 4/2004 | Evdokimov et al. | |
| 2004/0097559 A1 | 5/2004 | Warshakoon et al. | |
| 2004/0097560 A1 | 5/2004 | Warshakoon et al. | |
| 2005/0234045 A1 | 10/2005 | Warshakoon et al. | |
| 2005/0256126 A1 | 11/2005 | Warshakoon et al. | |
| 2007/0238722 A1 | 10/2007 | Warshakoon et al. | |
| 2007/0270407 A1 | 11/2007 | Warshakoon et al. | |
| 2007/0299116 A1 | 12/2007 | Gray et al. | |
| 2008/0004267 A1 | 1/2008 | Gray et al. | |
| 2008/0076764 A1 | 3/2008 | Peters et al. | |
| 2008/0108631 A1 | 5/2008 | Gray et al. | |
| 2009/0022715 A1 | 1/2009 | Rotello et al. | |
| 2009/0227639 A1 | 9/2009 | Gray et al. | |
| 2010/0016336 A1 | 1/2010 | Gray et al. | |
| 2010/0030487 A1 | 2/2010 | Evdokimov et al. | |
| 2010/0056610 A1 | 3/2010 | Peters et al. | |
| 2010/0069448 A1 | 3/2010 | Gray et al. | |
| 2010/0305097 A1 | 12/2010 | Warshakoon et al. | |
| 2011/0110961 A1 | 5/2011 | Gardner et al. | |
| 2011/0111058 A1 | 5/2011 | Shalwitz et al. | |
| 2011/0112055 A1 | 5/2011 | Gardner et al. | |
| 2011/0212951 A1 | 9/2011 | Gray et al. | |
| 2011/0268694 A1 | 11/2011 | Shalwitz et al. | |
| 2011/0274699 A1 | 11/2011 | Rotello et al. | |
| 2012/0077853 A1 | 3/2012 | Gray et al. | |

(Continued)

FOREIGN PATENT DOCUMENTS

| | | | |
|---|---|---|---|
| WO | WO 2004/043927 A1 | 5/2004 | |
| WO | WO 2004/043928 A2 | 5/2004 | |
| WO | WO 2007/116360 A2 | 10/2007 | |
| WO | WO 2007/150011 A2 | 12/2007 | |
| WO | WO 2008/002569 A2 | 1/2008 | |
| WO | WO 2008/002570 A2 | 1/2008 | |
| WO | WO 2008/002571 A2 | 1/2008 | |
| WO | WO 2010/081172 A1 | 7/2010 | |
| WO | WO 2011/005330 A1 | 1/2011 | |
| WO | WO 2011/057112 A1 | 5/2011 | |
| WO | WO 2011/057115 A1 | 5/2011 | |
| WO | WO 2011/057121 A1 | 5/2011 | |
| WO | WO 2012/047966 A2 | 4/2012 | |
| WO | WO 2013/056233 A1 | 4/2013 | |
| WO | WO 2013/056240 A1 | 4/2013 | |
| WO | WO 2014/145068 A1 | 9/2014 | |

OTHER PUBLICATIONS

U.S. Appl. No. 14/569,106, filed Dec. 12, 2014, Gray et al.

(Continued)

*Primary Examiner* — Sun Jae Yoo
(74) *Attorney, Agent, or Firm* — Wilson Sonsini Goodrich & Rosati

(57) ABSTRACT

Disclosed herein is a process for preparing N-benzyl-3-hydroxypyridin-2-(1H)-ones that are substituted at the pyridine ring 4-position with a 4-carbamoylpiperazin-1-yl moiety.

29 Claims, No Drawings

(56) References Cited

U.S. PATENT DOCUMENTS

| | | |
|---|---|---|
| 2012/0077975 A1 | 3/2012 | Gray et al. |
| 2012/0115876 A1 | 5/2012 | Warshakoon et al. |
| 2012/0128625 A1 | 5/2012 | Shalwitz et al. |
| 2012/0129847 A1 | 5/2012 | Peters et al. |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0158010 A1 | 6/2013 | Shalwitz et al. |
| 2013/0158045 A1 | 6/2013 | Gardner et al. |
| 2013/0324558 A1 | 12/2013 | Gray et al. |
| 2013/0331386 A1 | 12/2013 | Shalwitz et al. |
| 2014/0044707 A1 | 2/2014 | Rotello et al. |
| 2014/0066458 A1 | 3/2014 | Shalwitz et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2014/0364419 A1 | 12/2014 | Shalwitz et al. |
| 2015/0050277 A1 | 2/2015 | Peters et al. |
| 2015/0157617 A1 | 6/2015 | Shalwitz et al. |
| 2015/0218098 A1 | 8/2015 | Gardner et al. |

OTHER PUBLICATIONS

U.S. Appl. No. 14/627,463, filed Feb. 20, 2015, Peters et al.
U.S. Appl. No. 14/657,276, filed Mar. 13, 2015, Janusz et al.
U.S. Appl. No. 14/819,871, filed Aug. 6, 2015, Peters.
International search report and written opinion dated May 1, 2015 for PCT/US2015/016243.

PROCESS FOR PREPARING N-BENZYL-3-HYDROXY-4-SUBSTITUTED-PYRIDIN-2-(1H)-ONES

PRIORITY

This Application claims the benefit of priority from U.S. Provisional Patent Application Ser. No. 61/941,540, filed Feb. 19, 2014, the entirety of which is incorporated herein by reference.

FIELD OF THE DISCLOSURE

Disclosed herein is a process for preparing N-benzyl-3-hydroxypyridin-2-(1H)-ones that are substituted at the pyridine ring 4-position with a 4-carbamoylpiperazin-1-yl moiety.

DETAILED DISCLOSURE

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

The antecedent "about" indicates that the values are approximate. For example the range of "about 1 equivalent (equiv.) to about 50 equivalents" indicates that the values are approximate values. The range of "about 1 equivalent to about 50 equivalents" includes approximate and specific values, e.g., the range includes about 1 equivalent, 1 equivalent, about 50 equivalent and 50 equivalents.

When a range is described, the range includes both the endpoints of the range as well as all numbers in between. For example, "between 1 equiv. and 10 equiv." includes 1 equiv., 10 equiv. and all amounts between 1 equiv. and 10 equiv. Likewise, "from 1 equiv. to 10 equiv." includes 1 equiv., 10 equiv. and all amounts between 1 equiv. and 10 equiv.

Compounds

The present disclosure provides a process for the preparation of compounds having the general formula:

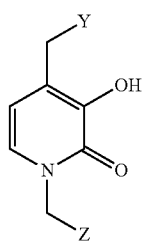

wherein Y is a 4-carbamoylpiperazin-1-yl unit having the formula:

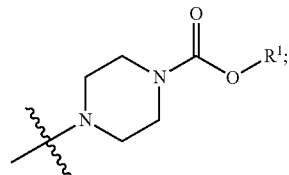

thereby providing a compound having the formula:

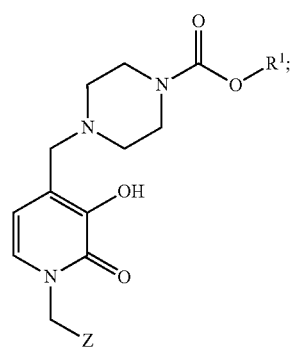

(I)

wherein $R^1$ is defined herein. Z is a substituted or unsubstituted phenyl ring having the formula:

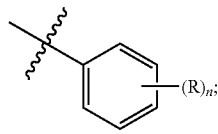

and
the index n is an integer from 0 to 5.

As such, the compounds that can be prepared by the disclosed process are also represented by the formula:

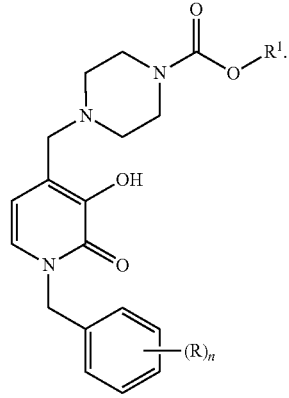

R units when present represent from 1 to 5 substitutions for a hydrogen atom on the indicated phenyl ring. As such, the index n is an integer from 1 to 5 when one or more substitutions are present. When the index n is 0, R is absent and therefore there are no substitutions for hydrogen and the resulting subgenus is represented by the formula:

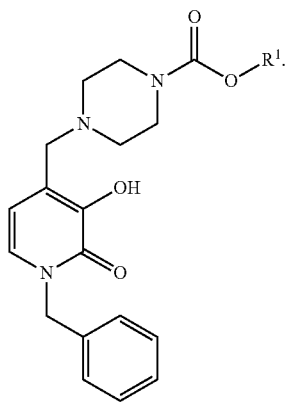

R Units

R units are independently chosen from:
i) $C_1$-$C_6$ linear, $C_3$-$C_6$ branched or $C_3$-$C_6$ cyclic alkyl. Non-limiting examples of $C_1$-$C_4$ linear alkyl units include methyl ($C_1$), ethyl ($C_2$), n-propyl ($C_3$), n-butyl ($C_4$), n-pentyl ($C_5$) and n-hexyl ($C_6$). Non-limiting examples of $C_3$-$C_6$ branched and $C_3$-$C_6$ cyclic alkyl units include iso-propyl ($C_3$), cyclopropyl ($C_3$), sec-butyl ($C_4$), iso-butyl ($C_4$), tert-butyl ($C_4$), cyclobutyl ($C_4$), neo-pentyl ($C_5$), cyclopentyl ($C_5$), iso-hexyl ($C_6$), cyclohexyl ($C_6$), and the like;
ii) $C_1$-$C_6$ linear, $C_3$-$C_6$ branched or $C_3$-$C_6$ cyclic alkoxy. Non-limiting examples of $C_1$-$C_4$ linear alkoxy units include methoxy ($C_1$), ethoxy ($C_2$), n-propoxy ($C_3$), n-butoxy ($C_4$), n-pentyloxy ($C_5$) and n-hexyloxy ($C_6$). Non-limiting examples of $C_3$-$C_6$ branched and $C_3$-$C_6$ cyclic alkoxy units include iso-propoxy ($C_3$), cyclopropoxy ($C_3$), sec-butoxy ($C_4$), iso-butoxy ($C_4$), tert-butoxy ($C_4$), cyclobutoxy ($C_4$), neopentyloxy ($C_5$), cyclopentyloxy ($C_5$), iso-hexyloxy ($C_6$), cyclohexyloxy ($C_6$), and the like;
iii) halogen, wherein each R unit comprising a halogen is independently chosen from fluoro, chloro, bromo or iodo; or
iv) cyano.

One aspect of the disclosure relates to compounds wherein the index n is equal to 0 and therefore R unit substitutions are absent therefore resulting in a subgenus having the formula:

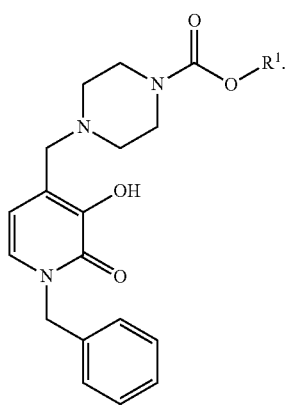

Another aspect of the disclosure relates to compounds wherein the index n is equal to 1. One embodiment of this aspect relates to compounds wherein R is a halogen. The following are non-limiting examples of this embodiment wherein Z units are chosen from 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, and 4-iodophenyl.

In one iteration of this embodiment, Z is 4-chlorophenyl.

Another embodiment of this aspect relates to compounds wherein R is chosen from one or more $C_1$-$C_6$ linear alkyl units. Non-limiting examples of this embodiment are Z units chosen from 2-methylphenyl, 3-methylphenyl, 4-methylphenyl, 2-ethylphenyl, 3-ethylphenyl, 4-ethylphenyl, 2-(n-propyl)phenyl, 3-(n-propyl)phenyl, 4-(n-propyl)phenyl, 2-(n-butyl)phenyl, 3-(n-butyl)phenyl, 4-(n-butyl)phenyl, 2-(n-pentyl)phenyl, 3-(n-pentyl)phenyl, 4-(n-pentyl)phenyl, 2-(n-hexyl)phenyl, 3-(n-hexyl)phenyl, and 4-(n-hexyl)phenyl.

A further embodiment of this aspect relates to compounds wherein R is chosen from one or more $C_3$-$C_6$ branched alkyl units. Non-limiting examples of this embodiment are Z unis chosen from 2-(iso-propyl)phenyl, 3-(iso-propyl)phenyl, 4-(iso-propyl)phenyl, 2-(iso-butyl)phenyl, 3-(iso-butyl)phenyl, 4-(iso-butyl)phenyl, 2-(sec-butyl)phenyl, 3-(sec-butyl)phenyl, 4-(sec-butyl)phenyl, 2-(tert-butyl)phenyl, 3-(tert-butyl)phenyl, 4-(tert-butyl)phenyl, 2-(iso-pentyl)phenyl, 3-(iso-pentyl)phenyl, 4-(iso-pentyl)phenyl, 2-(iso-hexyl)phenyl, 3-(iso-hexyl)phenyl, and 4-(iso-hexyl)phenyl.

A still further embodiment of this aspect relates to compounds wherein R is chosen from one or more $C_1$-$C_6$ linear alkoxy units. Non-limiting examples of this embodiment are Z unis chosen from 2-methoxyphenyl, 3-methoxyphenyl, 4-methoxyphenyl, 2-ethoxyphenyl, 3-ethoxyphenyl, 4-ethoxyphenyl, 2-(n-propoxy)phenyl, 3-(n-propoxy)phenyl, 4-(n-propoxy)phenyl, 2-(n-butoxy)phenyl, 3-(n-butoxy)phenyl, 4-(n-butoxy)phenyl, 2-(n-pentyloxy)phenyl, 3-(n-pentyloxy)phenyl, 4-(n-pentyloxy)phenyl, 2-(n-hexyloxy)phenyl, 3-(n-hexyloxy)phenyl, and 4-(n-hexyloxy)phenyl.

A yet further embodiment of this aspect relates to compounds wherein R is chosen from one or more $C_3$-$C_6$ branched alkoxy units. Non-limiting examples of this embodiment are Z unis chosen from 2-(iso-propoxy)phenyl, 3-(iso-propoxy)phenyl, 4-(iso-propoxy)phenyl, 2-(iso-butoxy)phenyl, 3-(iso-butoxy)phenyl, 4-(iso-butoxy)phenyl, 2-(sec-butoxy)phenyl, 3-(sec-butoxy)phenyl, 4-(sec-butoxy)phenyl, 2-(tert-butoxy)phenyl, 3-(tert-butoxy)phenyl, 4-(tert-butoxy)phenyl, 2-(iso-pentyloxy)phenyl, 3-(iso-pentyloxy)phenyl, 4-(iso-pentyloxy)phenyl, 2-(iso-hexyloxy)phenyl, 3-(iso-hexyloxy)phenyl, and 4-(iso-hexyloxy)phenyl.

A further aspect of the disclosure relates to compounds wherein the index n is greater than 1. One embodiment of this aspect relates to compounds wherein R is a halogen. The following are non-limiting examples of this embodiment wherein Z units are chosen from 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,4,6-trifluorophenyl, 3,4,5-trifluorophenyl, 2,3,4,5-tetrafluorophenyl, 2,3,4,6-tetra-fluorophenyl, 2,3,4,5,6-pentafluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,4,6-trichlorophenyl, 3,4,5-trichlorophenyl, 2,3,4,5-tetrachlorophenyl, 2,3,4,6-tetrachlorophenyl, 2,3,4,5,6-pentachlorophenyl, 2,3-dibromophenyl, 2,4-dibromophenyl, 2,5-dibromophenyl, 2,6-dibromophenyl, 3,4-dibromophenyl, 3,5-dibromophenyl, 2,3,4-tribromophenyl, 2,3,5-tribromophenyl, 2,4,6-tribromophenyl, 3,4,5-tribromophenyl, 2,3,4,5-tetrabromophenyl, 2,3,4,6-tetra-bromophenyl, 2,3,4,5,6-pentabromophenyl, 2,3-diiodophenyl, 2,4-diiodophenyl, 2,5- diiodophenyl, 2,6-diiodophenyl, 3,4-diiodophenyl, 3,5-diiodophenyl, 2,3,4-triiodophenyl, 2,3,5-triiodophenyl, 2,4,6-triiodophenyl, 3,4,5-triiodophenyl, 2,3,4,5-tetraiodophenyl, 2,3,4,6-tetra-iodophenyl, and 2,3,4,5,6-pentaiodophenyl.

Another embodiment of this aspect relates to compounds wherein R is a $C_1$-$C_6$ linear alkyl. The following are non-limiting examples of this embodiment wherein Z units are chosen from 2,3-dimethylphenyl, 2,4-dimethylphenyl, 2,5-dimethylphenyl, 2,6-dimethyl-phenyl, 3,4-dimethylphenyl, 3,5-dimethylphenyl, 2,3,4-trimethylphenyl, 2,3,5-trimethylphenyl, 2,4,6-trimethylphenyl, 3,4,5-trimethylphenyl, 2,3,4,5-tetramethylphenyl, 2,3,4,6-tetra-methylphenyl, 2,3,4,5,6-pentamethylphenyl, 2,3-diethylphenyl, 2,4-diethylphenyl, 2,5-diethylphenyl, 2,6-diethylphenyl, 3,4-diethylphenyl, 3,5-diethylphenyl, 2,3,4-triethylphenyl, 2,3,5-triethylphenyl, 2,4,6-triethylphenyl, 3,4,5-triethylphenyl, 2,3,4,5-tetraethylphenyl, 2,3,4,6-tetra-ethylphenyl, 2,3,4,5,6-pentaethylphenyl, 2,3-dibromophenyl, 2,4-dibromo-phenyl, 2,5-dibromophenyl, 2,6-dibromophenyl, 3,4-dibromophenyl, 3,5-dibromophenyl, 2,3,4-tri(n-propyl)phenyl, 2,3,5-tri(n-propyl)phenyl, 2,4,6-tri(n-propyl)phenyl, 3,4,5-tri(n-propyl)phenyl, 2,3,4,5-tetra(n-propyl)phenyl, 2,3,4,6-tetra-(n-propyl)phenyl, 2,3,4,5,6-penta(n-propyl)phenyl, 2,3-di(n-butyl)phenyl, 2,4-di(n-butyl)phenyl, 2,5-di(n-butyl)phenyl, 2,6-di(n-butyl)phenyl, 3,4-di(n-butyl)phenyl, 3,5-di(n-butyl)phenyl, 2,3,4-tri(n-butyl)-phenyl, 2,3,5-tri(n-butyl)phenyl, 2,4,6-tri(n-butyl)phenyl, 3,4,5-tri(n-butyl)phenyl, 2,3,4,5-tetra(n-butyl)phenyl, 2,3,4,6-tetra(n-butyl)phenyl, and 2,3,4,5,6-penta(n-butyl)phenyl.

A still further aspect of the disclosure relates to compounds wherein the index n is greater than 1 and wherein at least one R is chosen from $C_1$-$C_6$ linear, $C_3$-$C_6$ branched or $C_3$-$C_6$ cyclic alkyl and at least one R is chosen from halogen.

A yet further aspect of the disclosure relates to compounds wherein the index n is greater than 1 and wherein at least one R is chosen from $C_1$-$C_6$ linear, $C_3$-$C_6$ branched or $C_3$-$C_6$ cyclic alkoxy and at least one R is chosen from halogen.

A still yet further aspect of the disclosure relates to compounds wherein the index n is greater than 1 and wherein at least one R is chosen from $C_1$-$C_6$ linear, $C_3$-$C_6$ branched or $C_3$-$C_6$ cyclic alkyl and at least one R is chosen from $C_1$-$C_6$ linear, $C_3$-$C_6$ branched or $C_3$-$C_6$ cyclic alkoxy.

$R^1$ Units $R^1$ units are $C_1$-$C_4$ linear or $C_3$-$C_4$ branched alkyl. Non-limiting examples of $C_1$-$C_4$ linear alkyl units include methyl ($C_1$), ethyl ($C_2$), n-propyl ($C_3$), and n-butyl ($C_4$). Non-limiting examples of $C_3$-$C_6$ branched alkyl units include iso-propyl ($C_3$), sec-butyl ($C_4$), iso-butyl ($C_4$) and tert-butyl ($C_4$).

In one embodiment $R^1$ is tert-butyl.

In another embodiment $R^1$ is methyl.

In a further embodiment $R^1$ is ethyl.

The following are non-limiting examples of compounds that can be prepared by the disclosed process:

Methyl 4-((1-(2-fluorobenzyl)-3-hydroxy-2-oxo-1,2-dihydropyridin-4-yl)methyl)piperazine-1-carboxylate;

Methyl 4-((1-(3-fluorobenzyl)-3-hydroxy-2-oxo-1,2-dihydropyridin-4-yl)methyl)piperazine-1-carboxylate;

Methyl 4-((1-(4-fluorobenzyl)-3-hydroxy-2-oxo-1,2-dihydropyridin-4-yl)methyl)piperazine-1-carboxylate;

Methyl 4-((1-(2,3-difluorobenzyl)-3-hydroxy-2-oxo-1,2-dihydropyridin-4-yl)methyl)piperazine-1-carboxylate;

Methyl 4-((1-(2,4-difluorobenzyl)-3-hydroxy-2-oxo-1,2-dihydropyridin-4-yl)methyl)piperazine-1-carboxylate;

Methyl 4-((1-(2,5-difluorobenzyl)-3-hydroxy-2-oxo-1,2-dihydropyridin-4-yl)methyl)piperazine-1-carboxylate;

Methyl 4-((1-(2,6-difluorobenzyl)-3-hydroxy-2-oxo-1,2-dihydropyridin-4-yl)methyl)piperazine-1-carboxylate;

Methyl 4-((1-(3,4-difluorobenzyl)-3-hydroxy-2-oxo-1,2-dihydropyridin-4-yl)methyl)piperazine-1-carboxylate;

Methyl 4-((1-(3,5-difluorobenzyl)-3-hydroxy-2-oxo-1,2-dihydropyridin-4-yl)methyl)piperazine-1-carboxylate;

Methyl 4-((1-(2-chlorobenzyl)-3-hydroxy-2-oxo-1,2-dihydropyridin-4-yl)methyl)piperazine-1-carboxylate;

Methyl 4-((1-(3-chlorobenzyl)-3-hydroxy-2-oxo-1,2-dihydropyridin-4-yl)methyl)piperazine-1-carboxylate;

Methyl 4-((1-(4-chlorobenzyl)-3-hydroxy-2-oxo-1,2-dihydropyridin-4-yl)methyl)piperazine-1-carboxylate;

Methyl 4-((1-(2,3-dichlorobenzyl)-3-hydroxy-2-oxo-1,2-dihydropyridin-4-yl)methyl)piperazine-1-carboxylate;

Methyl 4-((1-(2,4-dichlorobenzyl)-3-hydroxy-2-oxo-1,2-dihydropyridin-4-yl)methyl)piperazine-1-carboxylate;

Methyl 4-((1-(2,5-dichlorobenzyl)-3-hydroxy-2-oxo-1,2-dihydropyridin-4-yl)methyl)piperazine-1-carboxylate;

Methyl 4-((1-(2,6-dichlorobenzyl)-3-hydroxy-2-oxo-1,2-dihydropyridin-4-yl)methyl)piperazine-1-carboxylate;

Methyl 4-((1-(3,4-dichlorobenzyl)-3-hydroxy-2-oxo-1,2-dihydropyridin-4-yl)methyl)piperazine-1-carboxylate;

Methyl 4-((1-(3,5-dichlorobenzyl)-3-hydroxy-2-oxo-1,2-dihydropyridin-4-yl)methyl)piperazine-1-carboxylate;

Methyl 4-((1-(2-bromobenzyl)-3-hydroxy-2-oxo-1,2-dihydropyridin-4-yl)methyl)piperazine-1-carboxylate;

Methyl 4-((1-(3-bromobenzyl)-3-hydroxy-2-oxo-1,2-dihydropyridin-4-yl)methyl)piperazine-1-carboxylate;

Methyl 4-((1-(4-bromobenzyl)-3-hydroxy-2-oxo-1,2-dihydropyridin-4-yl)methyl)piperazine-1-carboxylate;

Methyl 4-((1-(2,3-dibromobenzyl)-3-hydroxy-2-oxo-1,2-dihydropyridin-4-yl)methyl)piperazine-1-carboxylate;

Methyl 4-((1-(2,4-dibromobenzyl)-3-hydroxy-2-oxo-1,2-dihydropyridin-4-yl)methyl)piperazine-1-carboxylate;

Methyl 4-((1-(2,5-dibromobenzyl)-3-hydroxy-2-oxo-1,2-dihydropyridin-4-yl)methyl)piperazine-1-carboxylate;

Methyl 4-((1-(2,6-dibromobenzyl)-3-hydroxy-2-oxo-1,2-dihydropyridin-4-yl)methyl)piperazine-1-carboxylate;

Methyl 4-((1-(3,4-dibromobenzyl)-3-hydroxy-2-oxo-1,2-dihydropyridin-4-yl)methyl)piperazine-1-carboxylate;

Methyl 4-((1-(3,5-dibromobenzyl)-3-hydroxy-2-oxo-1,2-dihydropyridin-4-yl)methyl)piperazine-1-carboxylate;

Methyl 4-((1-(2-iodobenzyl)-3-hydroxy-2-oxo-1,2-dihydropyridin-4-yl)methyl)piperazine-1-carboxylate;

Methyl 4-((1-(3-iodobenzyl)-3-hydroxy-2-oxo-1,2-dihydropyridin-4-yl)methyl)piperazine-1-carboxylate;

Methyl 4-((1-(4-iodobenzyl)-3-hydroxy-2-oxo-1,2-dihydropyridin-4-yl)methyl)piperazine-1-carboxylate;

Methyl 4-((1-(2,3-diiodobenzyl)-3-hydroxy-2-oxo-1,2-dihydropyridin-4-yl)methyl)piperazine-1-carboxylate;

Methyl 4-((1-(2,4-diiodobenzyl)-3-hydroxy-2-oxo-1,2-dihydropyridin-4-yl)methyl)piperazine-1-carboxylate;

Methyl 4-((1-(2,5-diiodobenzyl)-3-hydroxy-2-oxo-1,2-dihydropyridin-4-yl)methyl)piperazine-1-carboxylate;

Methyl 4-((1-(2,6-diiodobenzyl)-3-hydroxy-2-oxo-1,2-dihydropyridin-4-yl)methyl)piperazine-1-carboxylate;

Methyl 4-((1-(3,4-diiodobenzyl)-3-hydroxy-2-oxo-1,2-dihydropyridin-4-yl)methyl)piperazine-1-carboxylate;

Methyl 4-((1-(3,5-diiodobenzyl)-3-hydroxy-2-oxo-1,2-dihydropyridin-4-yl)methyl)piperazine-1-carboxylate;

Ethyl 4-((1-(2-fluorobenzyl)-3-hydroxy-2-oxo-1,2-dihydropyridin-4-yl)methyl)piperazine-1-carboxylate;

Ethyl 4-((1-(3-fluorobenzyl)-3-hydroxy-2-oxo-1,2-dihydropyridin-4-yl)methyl)piperazine-1-carboxylate;

Ethyl 4-((1-(4-fluorobenzyl)-3-hydroxy-2-oxo-1,2-dihydropyridin-4-yl)methyl)piperazine-1-carboxylate;

Ethyl 4-((1-(2,3-difluorobenzyl)-3-hydroxy-2-oxo-1,2-dihydropyridin-4-yl)methyl)piperazine-1-carboxylate;

Ethyl 4-((1-(2,4-difluorobenzyl)-3-hydroxy-2-oxo-1,2-dihydropyridin-4-yl)methyl)piperazine-1-carboxylate;

Ethyl 4-((1-(2,5-difluorobenzyl)-3-hydroxy-2-oxo-1,2-dihydropyridin-4-yl)methyl)piperazine-1-carboxylate;

Ethyl 4-((1-(2,6-difluorobenzyl)-3-hydroxy-2-oxo-1,2-dihydropyridin-4-yl)methyl)piperazine-1-carboxylate;

Ethyl 4-((1-(3,4-difluorobenzyl)-3-hydroxy-2-oxo-1,2-dihydropyridin-4-yl)methyl)piperazine-1-carboxylate;

Ethyl 4-((1-(3,5-difluorobenzyl)-3-hydroxy-2-oxo-1,2-dihydropyridin-4-yl)methyl)piperazine-1-carboxylate;

Ethyl 4-((1-(2-chlorobenzyl)-3-hydroxy-2-oxo-1,2-dihydropyridin-4-yl)methyl)piperazine-1-carboxylate;

Ethyl 4-((1-(3-chlorobenzyl)-3-hydroxy-2-oxo-1,2-dihydropyridin-4-yl)methyl)piperazine-1-carboxylate;

Ethyl 4-((1-(4-chlorobenzyl)-3-hydroxy-2-oxo-1,2-dihydropyridin-4-yl)methyl)piperazine-1-carboxylate;

Ethyl 4-((1-(2,3-dichlorobenzyl)-3-hydroxy-2-oxo-1,2-dihydropyridin-4-yl)methyl)piperazine-1-carboxylate;

Ethyl 4-((1-(2,4-dichlorobenzyl)-3-hydroxy-2-oxo-1,2-dihydropyridin-4-yl)methyl)piperazine-1-carboxylate;

Ethyl 4-((1-(2,5-dichlorobenzyl)-3-hydroxy-2-oxo-1,2-dihydropyridin-4-yl)methyl)piperazine-1-carboxylate;

Ethyl 4-((1-(2,6-dichlorobenzyl)-3-hydroxy-2-oxo-1,2-dihydropyridin-4-yl)methyl)piperazine-1-carboxylate;

Ethyl 4-((1-(3,4-dichlorobenzyl)-3-hydroxy-2-oxo-1,2-dihydropyridin-4-yl)methyl)piperazine-1-carboxylate;

Ethyl 4-((1-(3,5-dichlorobenzyl)-3-hydroxy-2-oxo-1,2-dihydropyridin-4-yl)methyl)piperazine-1-carboxylate;

Ethyl 4-((1-(2-bromobenzyl)-3-hydroxy-2-oxo-1,2-dihydropyridin-4-yl)methyl)piperazine-1-carboxylate;

Ethyl 4-((1-(3-bromobenzyl)-3-hydroxy-2-oxo-1,2-dihydropyridin-4-yl)methyl)piperazine-1-carboxylate;

Ethyl 4-((1-(4-bromobenzyl)-3-hydroxy-2-oxo-1,2-dihydropyridin-4-yl)methyl)piperazine-1-carboxylate;

Ethyl 4-((1-(2,3-dibromobenzyl)-3-hydroxy-2-oxo-1,2-dihydropyridin-4-yl)methyl)piperazine-1-carboxylate;

Ethyl 4-((1-(2,4-dibromobenzyl)-3-hydroxy-2-oxo-1,2-dihydropyridin-4-yl)methyl)piperazine-1-carboxylate;

Ethyl 4-((1-(2,5-dibromobenzyl)-3-hydroxy-2-oxo-1,2-dihydropyridin-4-yl)methyl)piperazine-1-carboxylate;

Ethyl 4-((1-(2,6-dibromobenzyl)-3-hydroxy-2-oxo-1,2-dihydropyridin-4-yl)methyl)piperazine-1-carboxylate;

Ethyl 4-((1-(3,4-dibromobenzyl)-3-hydroxy-2-oxo-1,2-dihydropyridin-4-yl)methyl)piperazine-1-carboxylate;

Ethyl 4-((1-(3,5-dibromobenzyl)-3-hydroxy-2-oxo-1,2-dihydropyridin-4-yl)methyl)piperazine-1-carboxylate;

Ethyl 4-((1-(2-iodobenzyl)-3-hydroxy-2-oxo-1,2-dihydropyridin-4-yl)methyl)piperazine-1-carboxylate;

Ethyl 4-((1-(3-iodobenzyl)-3-hydroxy-2-oxo-1,2-dihydropyridin-4-yl)methyl)piperazine-1-carboxylate;

Ethyl 4-((1-(4-iodobenzyl)-3-hydroxy-2-oxo-1,2-dihydropyridin-4-yl)methyl)piperazine-1-carboxylate;

Ethyl 4-((1-(2,3-diiodobenzyl)-3-hydroxy-2-oxo-1,2-dihydropyridin-4-yl)methyl)piperazine-1-carboxylate;

Ethyl 4-((1-(2,4-diiodobenzyl)-3-hydroxy-2-oxo-1,2-dihydropyridin-4-yl)methyl)piperazine-1-carboxylate;

Ethyl 4-((1-(2,5-diiodobenzyl)-3-hydroxy-2-oxo-1,2-dihydropyridin-4-yl)methyl)piperazine-1-carboxylate;

Ethyl 4-((1-(2,6-diiodobenzyl)-3-hydroxy-2-oxo-1,2-dihydropyridin-4-yl)methyl)piperazine-1-carboxylate;

Ethyl 4-((1-(3,4-diiodobenzyl)-3-hydroxy-2-oxo-1,2-dihydropyridin-4-yl)methyl)piperazine-1-carboxylate;

Ethyl 4-((1-(3,5-diiodobenzyl)-3-hydroxy-2-oxo-1,2-dihydropyridin-4-yl)methyl)piperazine-1-carboxylate;

tert-Butyl 4-((1-(2-fluorobenzyl)-3-hydroxy-2-oxo-1,2-dihydropyridin-4-yl)methyl)piperazine-1-carboxylate;

tert-Butyl 4-((1-(3-fluorobenzyl)-3-hydroxy-2-oxo-1,2-dihydropyridin-4-yl)methyl)piperazine-1-carboxylate;

tert-Butyl 4-((1-(4-fluorobenzyl)-3-hydroxy-2-oxo-1,2-dihydropyridin-4-yl)methyl)piperazine-1-carboxylate;

tert-Butyl 4-((1-(2,3-difluorobenzyl)-3-hydroxy-2-oxo-1,2-dihydropyridin-4-yl)methyl)piperazine-1-carboxylate;

tert-Butyl 4-((1-(2,4-difluorobenzyl)-3-hydroxy-2-oxo-1,2-dihydropyridin-4-yl)methyl)piperazine-1-carboxylate;

tert-Butyl 4-((1-(2,5-difluorobenzyl)-3-hydroxy-2-oxo-1,2-dihydropyridin-4-yl)methyl)piperazine-1-carboxylate;

tert-Butyl 4-((1-(2,6-difluorobenzyl)-3-hydroxy-2-oxo-1,2-dihydropyridin-4-yl)methyl)piperazine-1-carboxylate;

tert-Butyl 4-((1-(3,4-difluorobenzyl)-3-hydroxy-2-oxo-1,2-dihydropyridin-4-yl)methyl)piperazine-1-carboxylate;

tert-Butyl 4-((1-(3,5-difluorobenzyl)-3-hydroxy-2-oxo-1,2-dihydropyridin-4-yl)methyl)piperazine-1-carboxylate;

tert-Butyl 4-((1-(2-chlorobenzyl)-3-hydroxy-2-oxo-1,2-dihydropyridin-4-yl)methyl)piperazine-1-carboxylate;

tert-Butyl 4-((1-(3-chlorobenzyl)-3-hydroxy-2-oxo-1,2-dihydropyridin-4-yl)methyl)piperazine-1-carboxylate;

tert-Butyl 4-((1-(4-chlorobenzyl)-3-hydroxy-2-oxo-1,2-dihydropyridin-4-yl)methyl)piperazine-1-carboxylate;

tert-Butyl 4-((1-(2,3-dichlorobenzyl)-3-hydroxy-2-oxo-1,2-dihydropyridin-4-yl)methyl)piperazine-1-carboxylate;

tert-Butyl 4-((1-(2,4-dichlorobenzyl)-3-hydroxy-2-oxo-1,2-dihydropyridin-4-yl)methyl)piperazine-1-carboxylate;

tert-Butyl 4-((1-(2,5-dichlorobenzyl)-3-hydroxy-2-oxo-1,2-dihydropyridin-4-yl)methyl)piperazine-1-carboxylate;

tert-Butyl 4-((1-(2,6-dichlorobenzyl)-3-hydroxy-2-oxo-1,2-dihydropyridin-4-yl)methyl)piperazine-1-carboxylate;

tert-Butyl 4-((1-(3,4-dichlorobenzyl)-3-hydroxy-2-oxo-1,2-dihydropyridin-4-yl)methyl)piperazine-1-carboxylate;

tert-Butyl 4-((1-(3,5-dichlorobenzyl)-3-hydroxy-2-oxo-1,2-dihydropyridin-4-yl)methyl)piperazine-1-carboxylate;

tert-Butyl 4-((1-(2-bromobenzyl)-3-hydroxy-2-oxo-1,2-dihydropyridin-4-yl)methyl)piperazine-1-carboxylate;

tert-Butyl 4-((1-(3-bromobenzyl)-3-hydroxy-2-oxo-1,2-dihydropyridin-4-yl)methyl)piperazine-1-carboxylate;

tert-Butyl 4-((1-(4-bromobenzyl)-3-hydroxy-2-oxo-1,2-dihydropyridin-4-yl)methyl)piperazine-1-carboxylate;

tert-Butyl 4-((1-(2,3-dibromobenzyl)-3-hydroxy-2-oxo-1,2-dihydropyridin-4-yl)methyl)piperazine-1-carboxylate;

tert-Butyl 4-((1-(2,4-dibromobenzyl)-3-hydroxy-2-oxo-1,2-dihydropyridin-4-yl)methyl)piperazine-1-carboxylate;

tert-Butyl 4-((1-(2,5-dibromobenzyl)-3-hydroxy-2-oxo-1,2-dihydropyridin-4-yl)methyl)piperazine-1-carboxylate;

tert-Butyl 4-((1-(2,6-dibromobenzyl)-3-hydroxy-2-oxo-1,2-dihydropyridin-4-yl)methyl)piperazine-1-carboxylate;

tert-Butyl 4-((1-(3,4-dibromobenzyl)-3-hydroxy-2-oxo-1,2-dihydropyridin-4-yl)methyl)piperazine-1-carboxylate;

tert-Butyl 4-((1-(3,5-dibromobenzyl)-3-hydroxy-2-oxo-1,2-dihydropyridin-4-yl)methyl)piperazine-1-carboxylate;

tert-Butyl 4-((1-(2-iodobenzyl)-3-hydroxy-2-oxo-1,2-dihydropyridin-4-yl)methyl)piperazine-1-carboxylate;

tert-Butyl 4-((1-(3-iodobenzyl)-3-hydroxy-2-oxo-1,2-dihydropyridin-4-yl)methyl)piperazine-1-carboxylate;

tert-Butyl 4-((1-(4-iodobenzyl)-3-hydroxy-2-oxo-1,2-dihydropyridin-4-yl)methyl)piperazine-1-carboxylate;

tert-Butyl 4-((1-(2,3-diiodobenzyl)-3-hydroxy-2-oxo-1,2-dihydropyridin-4-yl)methyl)piperazine-1-carboxylate;
tert-Butyl 4-((1-(2,4-diiodobenzyl)-3-hydroxy-2-oxo-1,2-dihydropyridin-4-yl)methyl)piperazine-1-carboxylate;
tert-Butyl 4-((1-(2,5-diiodobenzyl)-3-hydroxy-2-oxo-1,2-dihydropyridin-4-yl)methyl)piperazine-1-carboxylate;
tert-Butyl 4-((1-(2,6-diiodobenzyl)-3-hydroxy-2-oxo-1,2-dihydropyridin-4-yl)methyl)piperazine-1-carboxylate;
tert-Butyl 4-((1-(3,4-diiodobenzyl)-3-hydroxy-2-oxo-1,2-dihydropyridin-4-yl)methyl)piperazine-1-carboxylate;
tert-Butyl 4-((1-(3,5-diiodobenzyl)-3-hydroxy-2-oxo-1,2-dihydropyridin-4-yl)methyl)piperazine-1-carboxylate;
Methyl 4-((1-(2-methylbenzyl)-3-hydroxy-2-oxo-1,2-dihydropyridin-4-yl)methyl)piperazine-1-carboxylate;
Methyl 4-((1-(3-methylbenzyl)-3-hydroxy-2-oxo-1,2-dihydropyridin-4-yl)methyl)piperazine-1-carboxylate;
Methyl 4-((1-(4-methylbenzyl)-3-hydroxy-2-oxo-1,2-dihydropyridin-4-yl)methyl)piperazine-1-carboxylate;
Methyl 4-((1-(2,3-dimethylbenzyl)-3-hydroxy-2-oxo-1,2-dihydropyridin-4-yl)methyl)piperazine-1-carboxylate;
Methyl 4-((1-(2,4-dimethylbenzyl)-3-hydroxy-2-oxo-1,2-dihydropyridin-4-yl)methyl)piperazine-1-carboxylate;
Methyl 4-((1-(2,5-dimethylbenzyl)-3-hydroxy-2-oxo-1,2-dihydropyridin-4-yl)methyl)piperazine-1-carboxylate;
Methyl 4-((1-(2,6-dimethylbenzyl)-3-hydroxy-2-oxo-1,2-dihydropyridin-4-yl)methyl)piperazine-1-carboxylate;
Methyl 4-((1-(3,4-dimethylbenzyl)-3-hydroxy-2-oxo-1,2-dihydropyridin-4-yl)methyl)piperazine-1-carboxylate;
Methyl 4-((1-(3,5-dimethylbenzyl)-3-hydroxy-2-oxo-1,2-dihydropyridin-4-yl)methyl)piperazine-1-carboxylate;
Methyl 4-((1-(2-methoxybenzyl)-3-hydroxy-2-oxo-1,2-dihydropyridin-4-yl)methyl)piperazine-1-carboxylate;
Methyl 4-((1-(3-methoxybenzyl)-3-hydroxy-2-oxo-1,2-dihydropyridin-4-yl)methyl)piperazine-1-carboxylate;
Methyl 4-((1-(4-methoxybenzyl)-3-hydroxy-2-oxo-1,2-dihydropyridin-4-yl)methyl)piperazine-1-carboxylate;
Methyl 4-((1-(2,3-dimethoxybenzyl)-3-hydroxy-2-oxo-1,2-dihydropyridin-4-yl)methyl)piperazine-1-carboxylate;
Methyl 4-((1-(2,4-dimethoxybenzyl)-3-hydroxy-2-oxo-1,2-dihydropyridin-4-yl)methyl)piperazine-1-carboxylate;
Methyl 4-((1-(2,5-dimethoxybenzyl)-3-hydroxy-2-oxo-1,2-dihydropyridin-4-yl)methyl)piperazine-1-carboxylate;
Methyl 4-((1-(2,6-dimethoxybenzyl)-3-hydroxy-2-oxo-1,2-dihydropyridin-4-yl)methyl)piperazine-1-carboxylate;
Methyl 4-((1-(3,4-dimethoxybenzyl)-3-hydroxy-2-oxo-1,2-dihydropyridin-4-yl)methyl)piperazine-1-carboxylate;
Methyl 4-((1-(3,5-dimethoxybenzyl)-3-hydroxy-2-oxo-1,2-dihydropyridin-4-yl)methyl)piperazine-1-carboxylate;
Ethyl 4-((1-(2-methylbenzyl)-3-hydroxy-2-oxo-1,2-dihydropyridin-4-yl)methyl)piperazine-1-carboxylate;
Ethyl 4-((1-(3-methylbenzyl)-3-hydroxy-2-oxo-1,2-dihydropyridin-4-yl)methyl)piperazine-1-carboxylate;
Ethyl 4-((1-(4-methylbenzyl)-3-hydroxy-2-oxo-1,2-dihydropyridin-4-yl)methyl)piperazine-1-carboxylate;
Ethyl 4-((1-(2,3-dimethylbenzyl)-3-hydroxy-2-oxo-1,2-dihydropyridin-4-yl)methyl)piperazine-1-carboxylate;
Ethyl 4-((1-(2,4-dimethylbenzyl)-3-hydroxy-2-oxo-1,2-dihydropyridin-4-yl)methyl)piperazine-1-carboxylate;
Ethyl 4-((1-(2,5-dimethylbenzyl)-3-hydroxy-2-oxo-1,2-dihydropyridin-4-yl)methyl)piperazine-1-carboxylate;
Ethyl 4-((1-(2,6-dimethylbenzyl)-3-hydroxy-2-oxo-1,2-dihydropyridin-4-yl)methyl)piperazine-1-carboxylate;
Ethyl 4-((1-(3,4-dimethylbenzyl)-3-hydroxy-2-oxo-1,2-dihydropyridin-4-yl)methyl)piperazine-1-carboxylate;
Ethyl 4-((1-(3,5-dimethylbenzyl)-3-hydroxy-2-oxo-1,2-dihydropyridin-4-yl)methyl)piperazine-1-carboxylate;
Ethyl 4-((1-(2-methoxybenzyl)-3-hydroxy-2-oxo-1,2-dihydropyridin-4-yl)methyl)piperazine-1-carboxylate;
Ethyl 4-((1-(3-methoxybenzyl)-3-hydroxy-2-oxo-1,2-dihydropyridin-4-yl)methyl)piperazine-1-carboxylate;
Ethyl 4-((1-(4-methoxybenzyl)-3-hydroxy-2-oxo-1,2-dihydropyridin-4-yl)methyl)piperazine-1-carboxylate;
Ethyl 4-((1-(2,3-dimethoxybenzyl)-3-hydroxy-2-oxo-1,2-dihydropyridin-4-yl)methyl)piperazine-1-carboxylate;
Ethyl 4-((1-(2,4-dimethoxybenzyl)-3-hydroxy-2-oxo-1,2-dihydropyridin-4-yl)methyl)piperazine-1-carboxylate;
Ethyl 4-((1-(2,5-dimethoxybenzyl)-3-hydroxy-2-oxo-1,2-dihydropyridin-4-yl)methyl)piperazine-1-carboxylate;
Ethyl 4-((1-(2,6-dimethoxybenzyl)-3-hydroxy-2-oxo-1,2-dihydropyridin-4-yl)methyl)piperazine-1-carboxylate;
Ethyl 4-((1-(3,4-dimethoxybenzyl)-3-hydroxy-2-oxo-1,2-dihydropyridin-4-yl)methyl)piperazine-1-carboxylate;
Ethyl 4-((1-(3,5-dimethoxybenzyl)-3-hydroxy-2-oxo-1,2-dihydropyridin-4-yl)methyl)piperazine-1-carboxylate;
tert-Butyl 4-((1-(2-methylbenzyl)-3-hydroxy-2-oxo-1,2-dihydropyridin-4-yl)methyl)piperazine-1-carboxylate;
tert-Butyl 4-((1-(3-methylbenzyl)-3-hydroxy-2-oxo-1,2-dihydropyridin-4-yl)methyl)piperazine-1-carboxylate;
tert-Butyl 4-((1-(4-methylbenzyl)-3-hydroxy-2-oxo-1,2-dihydropyridin-4-yl)methyl)piperazine-1-carboxylate;
tert-Butyl 4-((1-(2,3-dimethylbenzyl)-3-hydroxy-2-oxo-1,2-dihydropyridin-4-yl)methyl)piperazine-1-carboxylate;
tert-Butyl 4-((1-(2,4-dimethylbenzyl)-3-hydroxy-2-oxo-1,2-dihydropyridin-4-yl)methyl)piperazine-1-carboxylate;
tert-Butyl 4-((1-(2,5-dimethylbenzyl)-3-hydroxy-2-oxo-1,2-dihydropyridin-4-yl)methyl)piperazine-1-carboxylate;
tert-Butyl 4-((1-(2,6-dimethylbenzyl)-3-hydroxy-2-oxo-1,2-dihydropyridin-4-yl)methyl)piperazine-1-carboxylate;
tert-Butyl 4-((1-(3,4-dimethylbenzyl)-3-hydroxy-2-oxo-1,2-dihydropyridin-4-yl)methyl)piperazine-1-carboxylate;
tert-Butyl 4-((1-(3,5-dimethylbenzyl)-3-hydroxy-2-oxo-1,2-dihydropyridin-4-yl)methyl)piperazine-1-carboxylate;
tert-Butyl 4-((1-(2-methoxybenzyl)-3-hydroxy-2-oxo-1,2-dihydropyridin-4-yl)methyl)piperazine-1-carboxylate;
tert-Butyl 4-((1-(3-methoxybenzyl)-3-hydroxy-2-oxo-1,2-dihydropyridin-4-yl)methyl)piperazine-1-carboxylate;
tert-Butyl 4-((1-(4-methoxybenzyl)-3-hydroxy-2-oxo-1,2-dihydropyridin-4-yl)methyl)piperazine-1-carboxylate;
tert-Butyl 4-((1-(2,3-dimethoxybenzyl)-3-hydroxy-2-oxo-1,2-dihydropyridin-4-yl)methyl)piperazine-1-carboxylate;
tert-Butyl 4-((1-(2,4-dimethoxybenzyl)-3-hydroxy-2-oxo-1,2-dihydropyridin-4-yl)methyl)piperazine-1-carboxylate;
tert-Butyl 4-((1-(2,5-dimethoxybenzyl)-3-hydroxy-2-oxo-1,2-dihydropyridin-4-yl)methyl)piperazine-1-carboxylate;
tert-Butyl 4-((1-(2,6-dimethoxybenzyl)-3-hydroxy-2-oxo-1,2-dihydropyridin-4-yl)methyl)piperazine-1-carboxylate;
tert-Butyl 4-((1-(3,4-dimethoxybenzyl)-3-hydroxy-2-oxo-1,2-dihydropyridin-4-yl)methyl)piperazine-1-carboxylate; and
tert-Butyl 4-((1-(3,5-dimethoxybenzyl)-3-hydroxy-2-oxo-1,2-dihydropyridin-4-yl)methyl)piperazine-1-carboxylate.

Process

The disclosed process is outlined herein below in Scheme I.

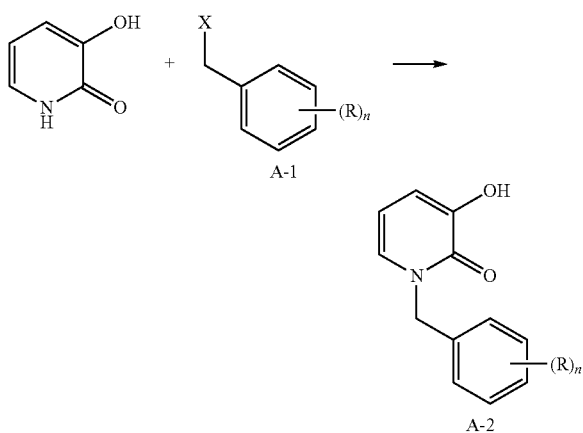

Scheme I

Step A

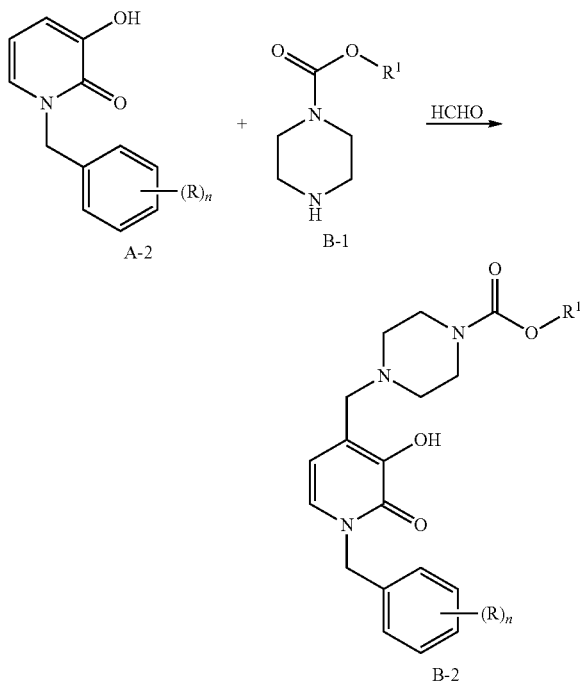

Step A

Step A relates to the benzylation of 3-hydroxypyridin-2(1H)-one (2,3-dihydroxy-pyridine) at the pyridin-2(1H)-one ring nitrogen with a benzylating agent having the formula:

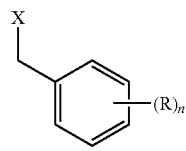

wherein X is a leaving group. Non-limiting examples of leaving groups include chloro, bromo, iodo, tosyl, mesyl and the like. R and the index n are defined herein above.

The reaction depicted in step A is carried out under modified Silyl-Hilbert-Johnson conditions. Without wishing to be limited by theory, the reaction depicted in Step A includes formation of di-silylated intermediate. This di-protected intermediate prevents undesired O-benzylation of the 3-hydroxy and 2-hydroxy units of the pyridine tautomeric form 3-hydroxypyridin-2(1H)-one by the benzylating agent A-1. The resulting bis-silyl protected intermediate has the formula:

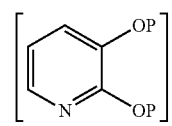

wherein P represents a silyl protecting group. Scheme II below summarizes a non-limiting example of Step A wherein two equivalents of hexamethyldisilazane are used to form intermediate A-i.

Scheme II

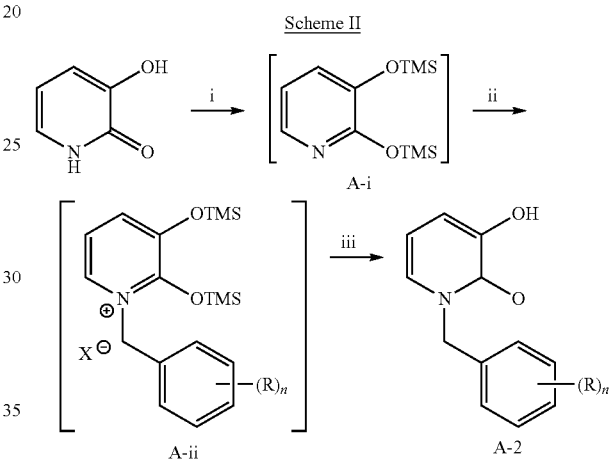

Step A(i) relates to the addition of at least about 2 equivalents of a silylating reagent to form a bis-O-silyl intermediate or a least one equivalent of a silylating reagent that can provide two equivalents of a silyl protecting group to form an intermediate such as A-i as depicted in the example set forth in Scheme II. In one non-limiting example, this intermediate can be formed by the reaction of bis(trimethylsilyl)amine (HMDS) with 3-hydroxypyridin-2(1H)-one. As indicated, intermediate A-i is not isolated, but is converted to intermediate A-ii in situ by the addition of reagent A-1 during step A(ii). Also as indicated in Scheme II, product A-ii is also not isolated. Aqueous work-up removes the silyl protecting groups allowing the pyridinium salt A-ii to collapse and tautomerize to the 3-hydroxy-pyridin-2(1H)-one form and thereby liberate N-benzyl-3-hydroxypyridin-2(1H)-ones having the formula A-2.

Step A can be conducted with any a silylating reagent in an amount wherein the agent provides two or more equivalents of protecting group. For example, one equivalent of hexamethyldisilazane provides two equivalents of a silyl protecting group. In one embodiment of the disclosed process, hexamethyldisilazane is used as the silylating reagent. Non-limiting examples of silylating reagents include trimethylsilyl chloride, tert-butyl dimethylsilyl chloride, trimethylsilylimidazole, N,O-bis(trimethylsilyl)acetamide, N,N'-bis(trimethylsilyl)urea, N,O-bis(trimethylsilyl)trifluoroacetamide, heptamethyldisilazane, 1,1,3,3,-tetramethyl-1,3-divinyl-disilizane, and the like.

Step A is conducted in the presence of a source of proton, i.e., a strong or weak protic acid as well as some salts of strong mineral acids. Typically the acid is present in a catalytic amount. In one embodiment, the source of proton is ammonium sulfate, $(NH_4)_2SO_4$. In another embodiment, the acid is hydroiodic, HI, or hydrobromic acid, HBr. In another embodiment the acid is phosphoric acid, $H_3PO_4$, or sulfuric acid, $H_2SO_4$.

Step A can be conducted in the presence of any compatible solvent or mixture of compatible solvents. Non-limiting examples of solvents includes acetonitrile, tetrahydrofuran, dichloromethane, chloroform, 1,2-dichloroethane, 1,1,1-trichloroethane, toluene, m-xylene and mixtures thereof. In one embodiment, acetonitrile is used as the solvent.

In one embodiment of the disclosed process, the reactant A-1 is activated toward nucleophilic attack by 3-hydroxypyridin-2(1H)-one. This is accomplished by replacing the original leaving group X with a leaving group $X^1$ which is more labile to attack by the 3-hydroxypyridin-2(1H)-one nitrogen. In one embodiment, an in situ Finkelstein reaction is used to activate the leaving group. A non-limiting example of the formation of an activated benzylating agent is depicted herein below in Scheme III.

Scheme III

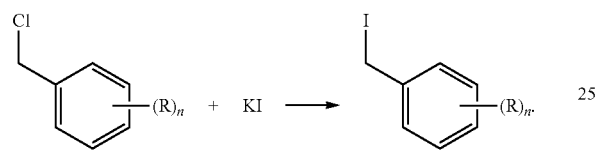

Step B

Step B relates to a Mannich Reaction between the N-benzyl-3-hydroxypyridin-2(1H)-one formed in Step A and a 4-carbamoylpiperazine, B-1. Step B is depicted in Scheme IV below.

Scheme IV

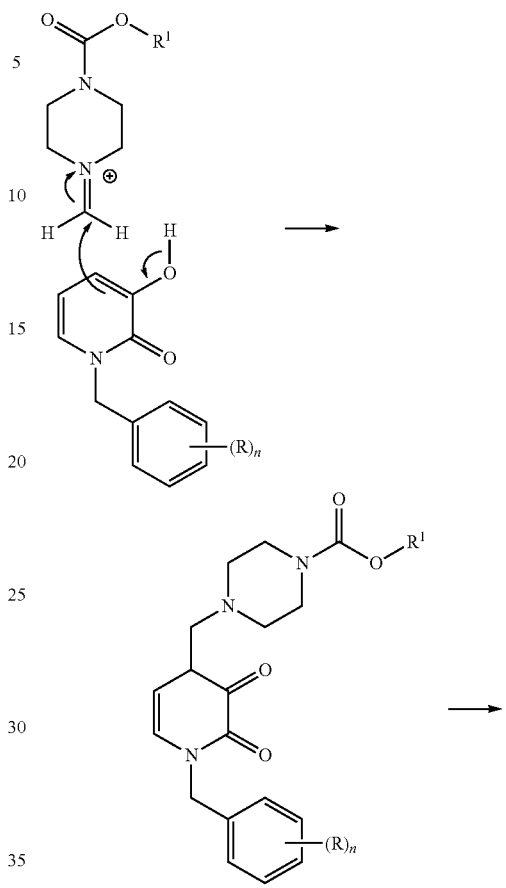

Without wishing to be limited by theory, Step B of the disclosed process involves the condensation of A-2 with B-1 in the presence of formaldehyde under standard Mannich Reaction conditions. The in situ generated imine of B-1 reacts with intermediate A-2 according to the proposed Scheme V herein below.

Scheme V

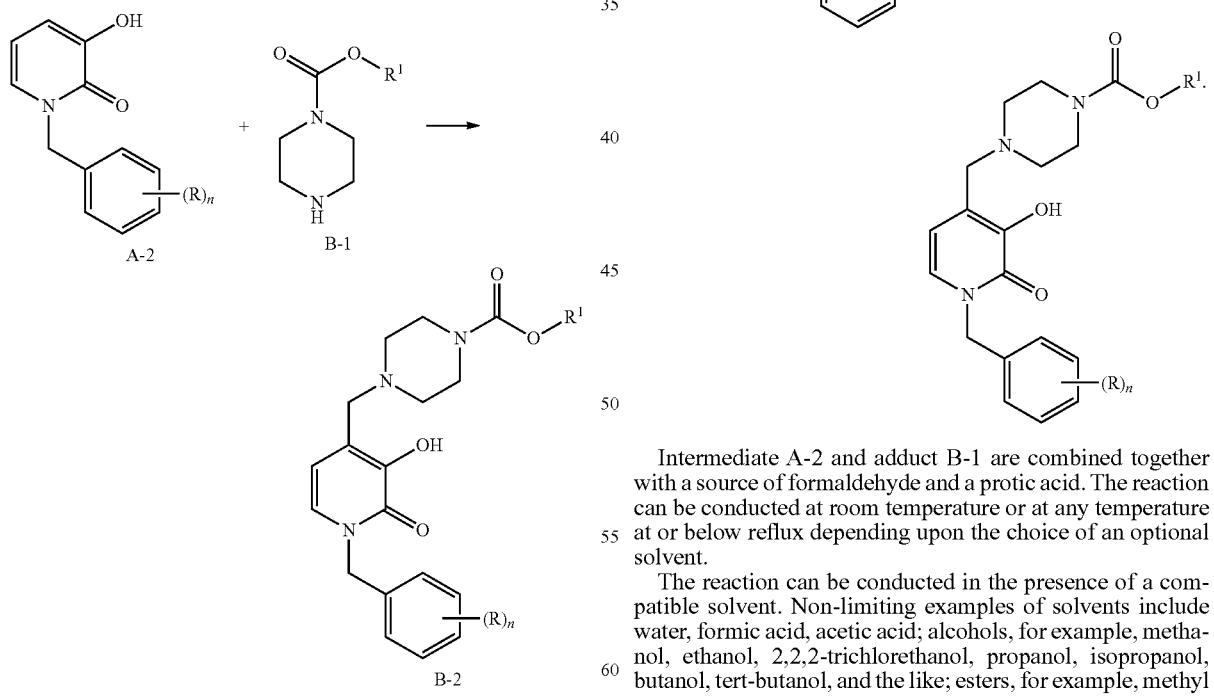

Intermediate A-2 and adduct B-1 are combined together with a source of formaldehyde and a protic acid. The reaction can be conducted at room temperature or at any temperature at or below reflux depending upon the choice of an optional solvent.

The reaction can be conducted in the presence of a compatible solvent. Non-limiting examples of solvents include water, formic acid, acetic acid; alcohols, for example, methanol, ethanol, 2,2,2-trichlorethanol, propanol, isopropanol, butanol, tert-butanol, and the like; esters, for example, methyl acetate, ethyl acetate, methyl propionate, ethyl propionate, and the like; ethers, for example, diethyl ether, methyl tert-butyl ether, tetrahydrofuran, dimethoxyethane, bis(2-methoxyethyl)ether(diglyme), 1,4-dioxane, and the like; alkanes, for example, pentane, isopentane, petroleum ether, hexane, mixtures of hexanes, cyclohexane, heptanes, isoheptane, octane, isooctane, and the like; halogenated solvents, for example, dichloromethane, chloroform, carbon tetrachloride, 1,1-dichloroethane, 1,1,1-trichloroethane, 1,2-dichloroethane, chlorobenzene, and the like; aromatic hydrocarbons, for example, benzene, toluene, 1,2-dimethylbenzene (ortho-xylene), 1,3-dimethylbenzene (meta-xylene), 1,4-dimetyl-benzene (para-xylene), nitrobenzene, and the like; dipolar aprotic solvents, for example, acetonitrile, dimethylsulfoxide, N,N-dimethylformamide, N,N-diethylformamide, N,N-dimethylacetamide, N,N-diethylacet-amide, N-methyl-2-pyrrolidinone, carbon disulfide, and hexamethylphosphoramide; and mixtures of one or more solvents.

In one embodiment of the disclosed process the solvent is an alcohol, for example, methanol, ethanol, n-propanol or iso-propanol. In one non-limiting example ethanol is used as a solvent. The formulator can choose different alcohols depending upon the desired temperature to which the reaction is heated, for example, the temperature of reflux.

In one embodiment of the disclosed process the source of formaldehyde is a 37% weight percent solution in water. Other reagents which form or release formaldehyde or a formaldehyde equivalent can be used.

The following is a non-limiting example of the disclosed process as outlined in Scheme VI and depicted in Example 1.

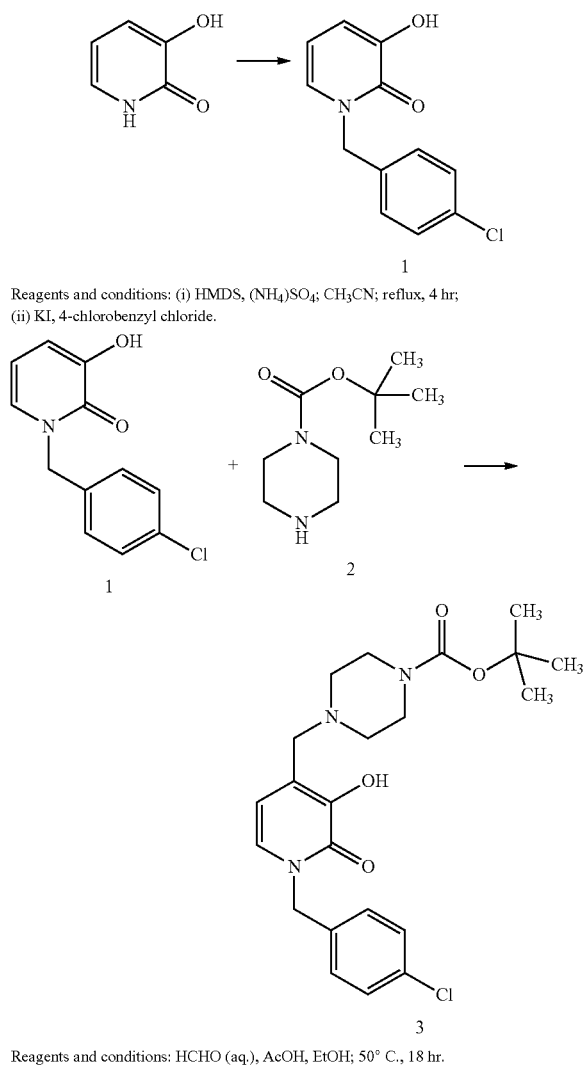

EXAMPLE 1 tert-Butyl 4-((1-(4-chlorobenzyl)-3-hydroxy-2-oxo-1,2-dihydropyridin-4-yl)methyl)piperazine-1-carboxylate (3)

Preparation of 1-(4-chlorobenzyl)-3-hydroxypyridin-2(1H)-one (1): to a nitrogen purged 1-L round bottom flask equipped with a mechanical stirrer, upright condenser, and thermometer was charged 3-hydroxypyridin-2(1H)-one [2,3-dihydroxypyridine] (40.0 g, 0.36 mol, 1 equiv.) [CAS No. 16867-04-2], ammonium sulfate (2.4 g, 0.02 mol, 0.05 equiv.) and acetonitrile (200 mL, 5 parts v/w). The resulting suspension was stirred at room temperature. Hexamethyldisilazane (116.2 g, 0.72 mol, 2 equiv.) is added dropwise. The resulting suspension was heated to reflux for 4 hours. The solution was then cooled to room temperature followed by the addition of a solution of 4-chlorobenzyl chloride (63.8 g, 0.4 mol, 1.1 equiv.) in acetonitrile (40 mL, 1 part v/w). Potassium iodide (59.8 g, 0.36 mol, 1 equiv.) is then added. The solution was then brought to reflux for 16 hours. The solution was cooled to 5° C. and water (240 mL) was slowly added over 15 minutes. The reaction mixture was allowed to warm to room temperature and stirring was continued for 2 hours. The solution was filtered under vacuum and rinsed with water (360 mL). The filter cake is then washed with methyl tert-butyl ether (360 mL). The resulting green-brown solid is vacuum dried to afford 63.5 g (86.2%) of the desired product. $^1$H NMR (DMSO-d$_6$) δ ppm 7.4 (d, 2H), 7.3 (d, 1H), 7.2 (d, 2H), 6.7 (d, 1H), 6.1 (t, 1H), and 5.1 (s, 2H).

Preparation of tert-butyl 4-((1-(4-chlorobenzyl)-3-hydroxy-2-oxo-1,2-dihydropyridin-4-yl)methyl)piperazine-1-carboxylate (3): to a nitrogen purged 2-L round bottom flask equipped with a mechanical stirrer, upright condenser, and thermometer was charged 1-(4-chlorobenzyl)-3-hydroxypyridin-2(1H)-one (1) (50.0 g, 0.21 mol, 1 equiv.), tert-butyl piperazine-1-carboxylate, (2) (79.0 g, 0.42 mol, 2 equiv.) [CAS No. 57260-71-6] and ethanol (750 mL, 15 parts v/w). The solution was stirred and 37% aqueous formaldehyde (34.7 mL, 0.47 mol, 2.2 equiv.) and acetic acid (36.4 mL, 0.64 mol, 3 equiv.) were added and the solution stirred for 1 hour after which the reaction solution was heated to 50° C. for 18 hours. The reaction mixture was then cooled below room temperature and filtered under vacuum. The resulting solid was rinsed with ethanol (250 mL) and dried under a stream of nitrogen to afford 77.2 g (83.9%) of the desired product. $^1$H NMR (DMSO-d$_6$) δ ppm 7.4 (d, 2H), 7.3 (d, 2H), 7.2 (d, 1H), 6.2 (d, 1H), 5.1 (s, 2H), 3.4-3.2 (m partly under brs water peak, 6H), 2.3 (m, 4H), 1.4 (s, 9H). $^{13}$C NMR (DMSO-d$_6$) [observed] δ ppm 157.24, 153.77, 144.36, 136.33, 132.15, 129.67, 128.48, 126.86, 124.56, 107.01, 78.74, 54.68, 52.49, 50.64, 43.48, and 28.03.

Other advantages which are obvious and which are inherent to the invention will be evident to one skilled in the art.

What is claimed is:
1. A process for preparing a compound, the process comprising:
A) reacting 3-hydroxypyridin-2(1H)-one with a benzylating agent having the formula:

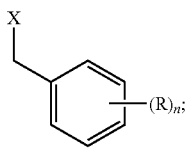

wherein X is a leaving group;
in the presence of:
   i) an amount of a silylating reagent that provides at least 2 equivalents of a silyl protecting group;
   ii) and a proton source;
to form a N-benzyl-3-hydroxypyridin-2(1H)-one having the formula:

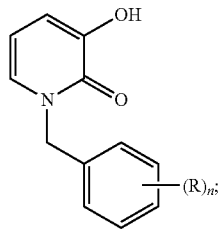

and

B) reacting the N-benzyl-3-hydroxypyridin-2(1H)-one formed in Step (A) with a compound having the formula:

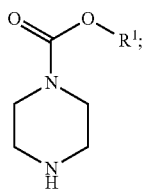

in the presence of a source of formaldehyde and an acid to form a product comprising a compound having the formula of Formula (I):

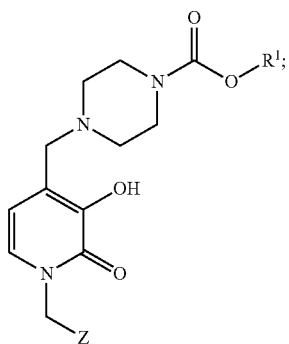

wherein Z is a substituted or unsubstituted phenyl ring having the formula:

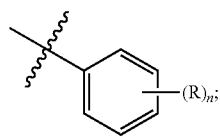

the index n is an integer from 0 to 5;
each R is independently:
i) alkyl;
ii) alkoxy;
iii) halogen; or
iv) cyano; and
$R^1$ is $C_1$-$C_4$ linear or $C_2$-$C_4$ branched alkyl.

2. The process according to claim 1, wherein $R^1$ is chosen from methyl, ethyl and tert-butyl.

3. The process according to claim 1, wherein $R^1$ is tert-butyl.

4. The process according to claim 1, wherein R is halogen.

5. The process according to claim 1, wherein Z is chosen from 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, and 4-iodophenyl.

6. The process according to claim 1, wherein Z is 4-chlorophenyl.

7. The process according to claim 1, wherein R is $C_1$-$C_6$ linear, $C_3$-$C_6$ branched or $C_3$-$C_6$ cyclic alkyl.

8. The process according to claim 1, wherein Z is chosen from 2-methylphenyl, 3-methylphenyl, 4-methylphenyl, 2-ethylphenyl, 3-ethylphenyl, 4-ethylphenyl, 2-(n-propyl)phenyl, 3-(n-propyl)phenyl, 4-(n-propyl)phenyl, 2-(n-butyl)phenyl, 3-(n-butyl)phenyl, 4-(n-butyl)phenyl, 2-(n-pentyl)phenyl, 3-(n-pentyl)phenyl, 4-(n-pentyl)phenyl, 2-(n-hexyl)phenyl, 3-(n-hexyl)phenyl, 4-(n-hexyl)phenyl, 2-(iso-propyl)phenyl, 3-(iso-propyl)phenyl, 4-(iso-propyl)phenyl, 2-(iso-butyl)phenyl, 3-(iso-butyl)phenyl, 4-(iso-butyl)phenyl, 2-(sec-butyl)phenyl, 3-(sec-butyl)phenyl, 4-(sec-butyl)phenyl, 2-(tert-butyl)phenyl, 3-(tert-butyl)phenyl, 4-(tert-butyl)phenyl, 2-(iso-pentyl)phenyl, 3-(iso-pentyl)phenyl, 4-(iso-pentyl)phenyl, 2-(iso-hexyl)phenyl, 3-(iso-hexyl)phenyl, and 4-(iso-hexyl)phenyl.

9. The process according to claim 1, wherein R is $C_1$-$C_6$ linear, $C_3$-$C_6$ branched or $C_3$-$C_6$ cyclic alkoxy.

10. The process according to claim 1, wherein Z is chosen from 2-methoxyphenyl, 3-methoxyphenyl, 4-methoxyphenyl, 2-ethoxyphenyl, 3-ethoxyphenyl, 4-ethoxyphenyl, 2-(n-propoxy)phenyl, 3-(n-propoxy)phenyl, 4-(n-propoxy)phenyl, 2-(n-butoxy)phenyl, 3-(n-butoxy)phenyl, 4-(n-butoxy)phenyl, 2-(n-pentyloxy)phenyl, 3-(n-pentyloxy)phenyl, 4-(n-pentyloxy)phenyl, 2-(n-hexyloxy)phenyl, 3-(n-hexyloxy)phenyl, 4-(n-hexyloxy)phenyl, 2-(iso-propoxy)phenyl, 3-(iso-propoxy)phenyl, 4-(iso-propoxy)phenyl, 2-(iso-butoxy)phenyl, 3-(iso-butoxy)phenyl, 4-(iso-butoxy)phenyl, 2-(sec-butoxy)phenyl, 3-(sec-butoxy)phenyl, 4-(sec-butoxy)phenyl, 2-(tert-butoxy)phenyl, 3-(tert-butoxy)phenyl, 4-(tert-butoxy)phenyl, 2-(iso-pentyloxy)phenyl, 3-(iso-pentyloxy)phenyl, 4-(iso-pentyloxy)phenyl, 2-(iso-hexyloxy)phenyl, 3-(iso-hexyloxy)phenyl, 4-(iso-hexyloxy)phenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,4,6-trifluorophenyl, 3,4,5-trifluorophenyl, 2,3,4,5-tetrafluorophenyl, 2,3,4,6-tetra-fluorophenyl, 2,3,4,5,6-pentafluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,4,6-trichlorophenyl, 3,4,5-trichlorophenyl, 2,3,4,5-tetrachlorophenyl, 2,3,4,6-tetra-chlorophenyl, 2,3,4,5,6-pentachlorophenyl, 2,3-dibromophenyl, 2,4-dibromophenyl, 2,5-dibromophenyl, 2,6-dibromophenyl, 3,4-dibromophenyl, 3,5-dibromophenyl, 2,3,4-tribromophenyl, 2,3,5-tribromophenyl, 2,4,6-tribromophenyl, 3,4,5-tribromophenyl, 2,3,4,5-tetrabromophenyl, 2,3,4,6-tetra-bromophenyl, 2,3,4,5,6-pentabromophenyl, 2,3-diiodophenyl, 2,4-diiodophenyl, 2,5-diiodophenyl, 2,6-diiodophenyl, 3,4-diiodophenyl, 3,5-diiodophenyl, 2,3,4-triiodophenyl, 2,3,5-triiodophenyl, 2,4,6-triiodophenyl, 3,4,5-triiodophenyl, 2,3,4,5-tetraiodophenyl, 2,3,4,6-tetraiodophenyl, 2,3,4,5,6-pentaiodophenyl, 2,3-dimethylphenyl, 2,4-dimethylphenyl, 2,5-dimethylphenyl, 2,6-dimethyl-phenyl, 3,4-dimethylphenyl, 3,5-dimethylphenyl, 2,3,4-trimethylphenyl, 2,3,5-trimethyl-phenyl, 2,4,6-trimethylphenyl, 3,4,5-trimethylphenyl, 2,3,4,5-tetramethylphenyl, 2,3,4,6-tetra-methylphenyl, 2,3, 4,5,6-pentamethylphenyl, 2,3-diethylphenyl, 2,4-diethylphenyl, 2,5-diethylphenyl, 2,6-diethylphenyl, 3,4-diethylphenyl, 3,5-diethylphenyl, 2,3,4-triethylphenyl, 2,3,5-triethylphenyl, 2,4,6-triethylphenyl, 3,4,5-triethylphenyl, 2,3,4,5-tetraethylphenyl, 2,3,4,6-tetra-ethylphenyl, 2,3,4,5,6-pentaethylphenyl, 2,3-dibromophenyl, 2,4-dibromo-phenyl, 2,5-dibromophenyl, 2,6-dibromophenyl, 3,4-dibromophenyl, 3,5-dibromophenyl, 2,3,4-tribromophenyl, 2,3,5-tri(n-propyl)phenyl, 2,4,6-tri(n-propyl)phenyl, 3,4,5-tri(n-propyl)phenyl, 2,3,4,5-tetra(n-propyl)phenyl, 2,3,4,6-tetra-(n-propyl)phenyl, 2,3,4,5,6-penta(n-propyl)phenyl, 2,3-di(n-butyl)phenyl, 2,4-di(n-butyl)phenyl, 2,5-di(n-butyl)phenyl, 2,6-di(n-butyl)phenyl, 3,4-di(n-butyl)phenyl, 3,5-di(n-butyl)phenyl, 2,3,4-tri(n-butyl)-phenyl, 2,3,5-tri(n-butyl)phenyl, 2,4,6-tri(n-butyl)phenyl, 3,4,5-tri(n-butyl)phenyl, 2,3,4,5-tetra(n-butyl)phenyl, 2,3,4,6-tetra(n-butyl)phenyl, and 2,3,4,5,6-penta(n-butyl)phenyl.

11. The process according to claim 1, wherein at least one R is chosen from $C_1$-$C_6$ linear, $C_3$-$C_6$ branched or $C_3$-$C_6$ cyclic alkyl and at least one R is halogen.

12. The process according to claim 1, wherein at least one R is chosen from $C_1$-$C_6$ linear, $C_3$-$C_6$ branched or $C_3$-$C_6$ cyclic alkoxy and at least one R is halogen.

13. The process according to claim 1, wherein at least one R is chosen from $C_1$-$C_6$ linear, $C_3$-$C_6$ branched or $C_3$-$C_6$ cyclic alkyl and at least one R is chosen from $C_1$-$C_6$ linear, $C_3$-$C_6$ branched or $C_3$-$C_6$ cyclic alkoxy.

14. The process according to claim 1, wherein the benzylating agent has the formula:

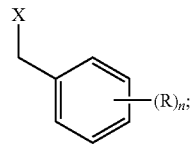

wherein the leaving group X is chosen from chloro, bromo, iodo, tosyl, and mesyl.

15. The process according claim 14, wherein the leaving group X is chloro.

16. The process according claim 14, wherein the leaving group X is iodo.

17. The process according to claim 1, wherein the number of equivalents of silylating reagent in Step (A) is from 2 to about 4.

18. The process according to claim 1, wherein the proton source in Step (A) is ammonium sulfate.

19. The process according to claim 1, wherein the source of formaldehyde is an aqueous solution of formaldehyde.

20. A process for preparing tert-butyl 4-((1-(4-chlorobenzyl)-3-hydroxy-2-oxo-1,2-dihydropyridin-4-yl)methyl)piperazine-1-carboxylate, comprising, A) reacting 3-hydroxypyridin-2(1H)-one having the formula:

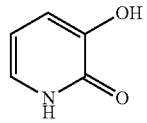

with 4-chlorobenzyl chloride having the formula:

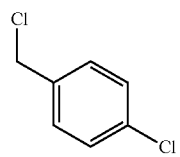

in the presence of two equivalents of a silylating reagent, a proton source and a salt of a mineral acid to form 1-(4-chlorobenzyl)-3-hydroxypyridin-2(1H)-one having the formula:

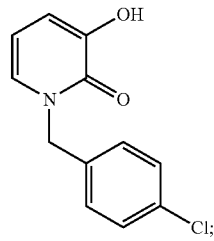 [SMILES: O=c1c(O)cccn1Cc1ccc(Cl)cc1]

and

B) reacting 1-(4-chlorobenzyl)-3-hydroxypyridin-2(1H)-one with tert-butyl piperazine-1-carboxylate having the formula:

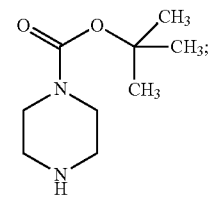

in the presence of aqueous formaldehyde and an a protic acid to form a product comprising tert-butyl 4-((1-(4-chlorobenzyl)-3-hydroxy-2-oxo -1,2-dihydropyridin-4-yl)methyl)piperazine-1 -carboxylate having the formula:

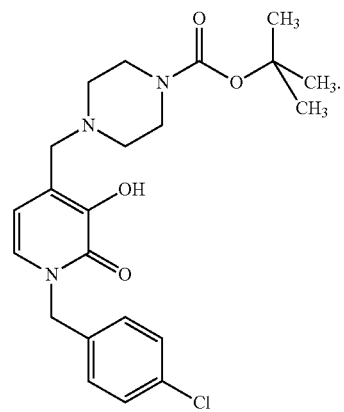 [SMILES: CC(C)(C)OC(=O)N1CCN(Cc2ccn(Cc3ccc(Cl)cc3)c(=O)c2O)CC1]

21. The process according to claim 20, wherein the silylating reagent is hexamethyldisilazane.

22. The process according to claim 20, wherein the proton source in Step (A) is ammonium sulfate.

23. The process according to claim 20, wherein the protic acid in Step (B) is acetic acid.

24. The process according to claim 20, wherein the salt of a mineral acid is potassium iodide.

25. The process according to claim 20, wherein the product further comprises acetate.

26. The process according to claim 1, wherein $R^1$ is $C_1$-$C_4$ linear or $C_3$-$C_4$ branched alkyl.

27. The process according to claim 1, wherein the product further comprises acetate.

28. The process according to claim 1, wherein the silylating reagent is hexamethyldisilazane.

29. The process according to claim 1, wherein the acid in Step (B) is acetic acid.

* * * * *